US008784373B2

(12) United States Patent
Gharib et al.

(10) Patent No.: US 8,784,373 B2
(45) Date of Patent: Jul. 22, 2014

(54) DRUG DELIVERY BY CARBON NANOTUBE ARRAYS

(75) Inventors: Morteza Gharib, Altadena, CA (US); Adrianus Indrat Aria, Pasadena, CA (US); Masoud Beizai, Laguna Hills, CA (US)

(73) Assignee: California Institute of Technology, Pasadena, CA (US)

( * ) Notice: Subject to any disclaimer, the term of this patent is extended or adjusted under 35 U.S.C. 154(b) by 45 days.

(21) Appl. No.: 13/224,287

(22) Filed: Sep. 1, 2011

(65) Prior Publication Data
US 2012/0058170 A1 Mar. 8, 2012

Related U.S. Application Data

(60) Provisional application No. 61/379,701, filed on Sep. 2, 2010.

(51) Int. Cl.
*A61M 31/00* (2006.01)
*A61M 37/00* (2006.01)

(52) U.S. Cl.
USPC .................. 604/103.01; 604/103.06; 604/509

(58) Field of Classification Search
USPC ............................... 604/103.01, 103.06, 509
See application file for complete search history.

(56) References Cited

U.S. PATENT DOCUMENTS

| | | | |
|---|---|---|---|
| 4,842,390 A | 6/1989 | Sottini et al. | |
| 5,116,317 A | 5/1992 | Carson, Jr. et al. | |
| 7,491,628 B2 | 2/2009 | Noca et al. | |
| 2005/0100960 A1* | 5/2005 | Dai et al. | 435/7.1 |
| 2006/0184112 A1* | 8/2006 | Horn et al. | 604/103.08 |
| 2008/0145616 A1 | 6/2008 | Gharib et al. | |
| 2011/0045080 A1* | 2/2011 | Powis et al. | 424/489 |

OTHER PUBLICATIONS

Anderson, A., et al., "High sensitivity assays for docetaxel and paclitaxel in plasma using solid-phase extraction and high-performance liquid chromatography with UV detection", BMC Clinical Pharmacology, Jan. 2006, vol. 6, Issue 2, pp. 1-10.
Arakawa, K., et al., "Fluorescence Analysis of Biochemical Constituents Identifies Atherosclerotic Plaque With a Thin Fibrous Cap", Arterioscler. Thromb. Vasc. Biol., 2002, vol. 22, pp. 1002-1007.
Arafin, D.Y., et al., "Role of Convective Row in Carmustine Delivery to a Brain Tumor", Pharmaceutical Research, 2009, pp. 1-14.
Celermajer, D.S., "Understanding the pathophysiology of the arterial wall: which method should we choose?", European Heart Journal Supplements, 2002, vol. 4, Supplement F, pp. F24-F28.
Creel, C. J., et al., "Arterial Paclitaxel Distribution and Deposition", Circulation Research, 2000, vol. 86, pp. 879-884.
Davies, M.J., "The Composition of Coronary-Artery Plaques", The New England Journal of Medicine, 1997, vol. 336, No. 18, pp. 1312-1314.
Detter, C., et al., "Fluorescent Cardiac Imaging: A Novel Intraoperative Method for Quantitative Assessment of Myocardial Perfusion During Graded Coronary Artery Stenosis", Circulation, 2007, vol. 116, pp. 1007-1014.
Diaz, J.F., et al., "Macromolecular Accessibility of fluorescent Taxoids Bound at a Paclitaxel Binding Site in the Microtubule Surface", J. Biol. Chem., 2005, vol. 280, No. 5, pp. 3928-3937.
Hattori, H., et al., "A Novel Real-Time Fluorescent Optical Imaging System in Mouse Heart, A Powerful Tool'for Studying Coronary Circulation and Cardiac Function", Circ Cardiovasc Imaging, 2009, vol. 2, pp. 277-278.
Hearn, E.M., et al., "Transmembrane passage of hydrophobic compounds through a protein channel wall", Nature, 2009, vol. 458, pp. 367-371.
Hosono, M. et al., "Intraoperative fluorescence imaging during surgery for coronary artery fistula", Interact CardioVasc Thorac Surg, 2010, vol. 10, pp. 476-477.
Lovich, M.A., et al., "Carrier Proteins Determine Local Pharmacokinetics and Arterial Distribution of Paclitaxel", J. Pharm. Sci., 2001, vol. 90, No. 9, pp. 1324-1335.
Migliavacca, F., et al., "Expansion and drug elution model of a coronary stent", Comput Methods Biomech Biomed Engin, 2007, vol. 10, No. 1, pp. 63-73.
Oreopoulos, J., et al., "Combinatorial microscopy for the study of protein-membrane interactions in supported lipid bilayers: Order parameter measurements by combined polarized TIRFM/AFM", J. Struct. Biol., 2009, vol. 168, pp. 21-36.
Panchagnula, R., et al., "Effect of Lipid Bilayer Alteration on Transdermal Delivery of a High-Molecular-Weight and Lipophilic Drug: Studies with Paclitaxel". J. Pharm. Sci., 2004, vol. 93, No. 9, pp. 2177-2183.
Parekh, H., et al., "The Transport and Binding of Taxol", Gen. Pharmac., 1997, vol. 29, No. 2, pp. 167-172.
Scheller, B., et al., "Paclitaxel Balloon Coating, a Novel Method for Prevention and Therapy of Restenosis", Circulation, 2004, vol. 110, pp. 810-814.
Tanaka, E., et al., "Real-Time Assessment of Cardiac Perfusion, Coronary Angiography, and Acute Intravascular Thrombi Using Dual- Channel Near-Infrared Fluorescence Imaging", Thorac Cardiovasc Surg., 2009, vol. 138, No. 1, pp. 133-140.
Tepe, G., et al., "Paclitaxel-coated Angioplasty Catheters for Local Drug Delivery", Touch Briefings—Interventional Cardiology, 2007, pp. 61-63.
Waseda, K., et al., "Intraoperative Fluorescence Imaging System for On-Site Assessment of Off-Pump Coronary Artery Bypass Graft", JACC: CardioVasc Imaging, 2009, vol. 2, No. 5, pp. 604-612.
Zilberman, M., et al., "Paclitaxel-eluting composite fibers: Drug release and tensile mechanical properties", J. Biomed. Mater. Res., 2008, vol. 84A, pp. 313-323.
Bronikowski, M.J., "Longer Nanotubes at Lower Temperatures: The Influence of Effective Activation Energies on Carbon Nanotube Growth by Thermal Chemical Vapor Deposition", J. Phys. Chem. C, 2007, vol. 111, No. 48, pp. 17705-17712.
Chen, Chuan-Hua, et al., "Dropwise condensation on superhydrophobic surfaces with two-tier roughness", Appl. Phys. Ltrs., 2007, vol. 90, pp. 173108-1-173108-3.

(Continued)

*Primary Examiner* — Gina C Justice
(74) *Attorney, Agent, or Firm* — One LLP

(57) ABSTRACT

The invention generally relates to carbon nanotube based drug delivery methods, devices, and compositions. More particularly, the invention relates to controlled drug delivery using anchored carbon nanotube arrays.

11 Claims, 19 Drawing Sheets

(56) References Cited

OTHER PUBLICATIONS

Figure 1A:
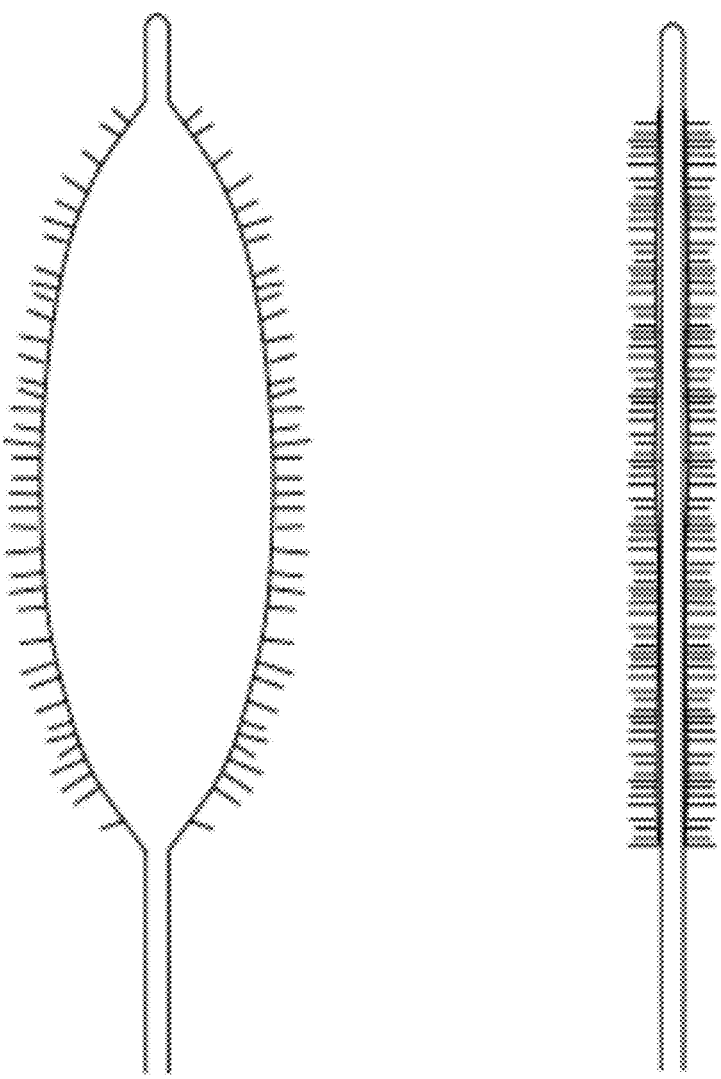

Chen, J., et al., "Functionalized Single-Wailed Carbon Nanotubes as Rationally Designed Vehicles for Tumor-Targeted Drug Delivery", J. Am. Chem. Soc., 2008, vol. 130, pp. 16778-16785.

Correa-Duarte, M.A., et al., "Fabrication and Biocompatibility of Carbon Nanotube-Based 3D Networks as Scaffolds for Cell Seeding and Growth", Nano Letters, 2004, vol. 4, No. 11, pp. 2233-2236.

Cui, D., et al., "Effect of single wall carbon nanotubes on human HEK293 cells", Toxicology Letters, 2005, vol. 155, pp. 73-85.

Daraio, C., et al., "Highly nonlinear contact interaction and dynamic energy dissipation by forest of carbon nanotubes", Appl. Phys. Ltrs., vol. 85, No. 23, pp. 5724-5726.

Elias, K.L., et al., "Enhanced functions of osteoblasts on nanometer diameter carbon fibers", Biomaterials, 2002, vol. 23, pp. 3279-3287.

Futaba, D.N., et al., "Shape-engineerable and highly densely packed single-walled carbon nanotubes and their application as super-capacitor electrodes", Nature Materials, 2006, vol. 5, pp. 987-994.

Gabay, T., et al., Engineered self-organization of neural networks using carbon nanotube clusters Physica A, 2005, vol. 350, pp. 611-621.

Hu, Hui, et al., "Chemically Functionalized Carbon Nanotubes as Substrates for Neuronal Growth", Nano. Lett., Mar. 2004, vol. 4, Issue 3, pp. 507-511.

McKenzie, Janice L., et al., "Decreased functions of astrocytes on carbon nanofiber materials", Biomaterials, 2004, vol. 25, pp. 1309-1317.

Glazachev, Y.I., "Fluorescence Photobleaching Recovery Method with Pulse-Position Modulation of Bleaching/Probing irradiation", J. Fluoresc., 2009, vol. 19, No. 5, pp. 875-880.

Holzapfel, G.A., et al., "Anisotropic Mechanical Properties of Tissue Components in Human Atherosclerotic Plaques", J. Bio. Eng., 2004, vol. 126, pp. 657-665.

Huang, X., et al., "Inherent-opening-controlled pattern formation in carbon nanotube arrays", Nanotechnology, 2007, vol. 18, pp. 1-6.

Huczko, A., et al., "Carbon Nanotubes: Experimental Evidence for a Null Risk of Skin Irritation and Allergy?", Fullerene Science and Technology, 2001, vol. 9, No. 2, pp. 247-250.

Huczko, A., et al., "Physiological Testing of Carbon Nanotubes: Are They Asbestos-Like?", Fullerene Science and Technology, 2001, vol. 9, No. 2, pp. 251-254.

Huczko, A., et al., "Pulmonary Toxicity of 1-D Nanocarbon Materials", Fullerenes, Nanotubes, and Carbon Nonostructures, 2005, vol. 13, pp. 141-145.

Ijima, S., "Helical microtubules of graphitic carbon", Nature, 1991, vol. 354, pp. 56-58.

Jia, G., et al., "Cytotoxicity of Carbon Nanomaterials: Single-Wall Nanotube, Multi-Wall Nanotube, and Fullerene", Environ. Sci. Technol., 2005, vol. 39, pp. 1378-1383.

Kopterides, P., et al., "Statins for sepsis: a critical and updated review", Clin Microbiol Infect, 2009, vol. 15, No. 4, pp. 325-334.

Krishnan, A., et al., "Young's modulus of single-walled nanotubes", Physical Review B, 1998, vol. 58, No. 20, pp. 14013-14015.

Lam, C.W., et al., "Pulmonary Toxicity of Single-Wall Carbon Nanotubes in Mice 7 and 90 Days After Intratracheal Instillation", Toxicol Sciences, 2004, vol. 77, pp. 126-134.

Liu, Z., et al., "Drug delivery with carbon nanotubes for in vivo cancer treatment", Cancer Res., 2008, vol. 68, No. 16, pp. 6652-6660.

Manohara, H.M., et al., "High-current-density field emitters based on arrays of carbon nanotube bundles", J. Vac. Sci. Tech B, 2005, vol. 23, No. 1, pp. 157-161.

Monteiro-Riviere, N.A., et al., "Multi-walled carbon nanotube interactions with human epidermal keratinocytes", Toxicol Letters, 2005, vol. 155, pp. 377-384.

Muller, J., et al., "Respiratory toxicity of multi-wall carbon nanotubes", Toxicol Appl Pharmacol, 2005, vol. 207, pp. 221-231.

Nessim, G.D., et al., "Tuning of Vertically-Aligned Carbon Nanotube Diameter and Area Density through Catalyst Pre-Treatment", Nano Letters., 2008, vol. 8, No. 11, pp. 3587-3593.

Pernodet, N., et al., "Pore size of agarose gels by atomic force microscopy", Electrophoresis, 1997, vol. 18, pp. 55-58.

Prausnitz, M.R., et al., "Transdermal drug delivery", Nature Biotechnology, 2008, vol. 26, No. 11, pp. 1261-1268.

Price, R.L., et al., "Selective bone cell adhesion on formulations containing carbon nanofibers", Biomaterials, 2003, vol. 24, pp. 1877-1887.

Sansom, E.B., et al., "Controlled partial embedding of carbon nanotubes within flexible transparent layers", Nanotechnology, 2008, vol. 19, pp. 1-6.

Scheuplein, R.J., et al., "Permeability of the Skin", Physiological Reviews, 1971, vol. 51, No. 4, pp. 702-747.

Scheuplein, R.J., Chapter 19: Permeability of the skin, Handbook of Physiology—Reactions to Environmental Agents, 2011, pp. 299-322.

Shvedova, A.A., et al., "Exposure to Carbon Nanotube Material: Assessment of Nanotube Cytotoxicity Using Human Keratinocyte Cells", J. Toxicol. Environ. Health, Pat A, 2003, vol. 66, pp. 1909-1926.

Tamura, K., et al., "Effects of Micro/Nano Particle Size on Cell Function and Morphology", Key Engineering Materials, 2004, Vols. 254-256, pp. 919-922.

Veedu, V.P., et al., "Multifunctional composites using reinforced laminae with carbon-nanotube forests", Nature Materials, 2006, vol. 5, pp. 457-462.

Wang, G.X., et al., "Growth and Lithium Storage Properties of Vertically Aligned Carbon Nanotubes", Metals and Materials Intl, 2006, vol. 12, No. 5, pp. 413-416.

Wardle, B.L., et al., "Fabrication and Characterization of Ultrahigh-Volume-Fraction Aligned Carbon Nanotube-Polymer Composites", Adv. Mater., 2008, vol. 20, pp. 2707-2714.

Warheit, D.B., et al., "Comparative Pulmonary Toxicity Assessment of Single-wall Carbon Nanotubes in Rats", Toxicol. Sciences, 2004, vol. 77, pp. 117-125.

Webster, T.J., et al., "Nano-biotechnology: carbon nanofibres as improved neural and orthopaedic implants", Nanotechnology, 2004, vol. 15, pp. 48-54.

Wermeling, D.P., et al., "Microneedles permit transdermal delivery of a skin-impermeant medication to humans", PNAS, 2008, vol. 105, No. 6, pp. 2058-2063.

Wong, E.W., et al., "Nanobeam Mechanics: Elasticity, Strength, and Toughness of Nanorods and Nanotubes", Science, 1997, vol. 277, pp. 1971-1975.

Wu, W., et al., "Covalently Combining Carbon Nanotubes with Anticancer Agent: Preparation and Antitumor Activity", ACS Nano, 2009, vol. 3, No. 9, pp. 2740-2750.

Xu, J., et al., "Enhanced Thermal Contact Conductance Using Carbon Nanotube Array Interfaces", IEEE Transactions on Components and Packaging Technologies, 2006, vol. 29, No. 2, pp. 261-267.

Yang, D, et al., "Hydrophilic multi-walled carbon nanotubes decorated with magnetite nanoparticles as lymphatic targeted drug delivery vehicles", Chem. Commun., 2009, pp. 4447-4449.

Yurdumakan, B., et al., "Synthetic gecko foot-hairs from multiwalled carbon nanotubes", Chem. Commun., 2005, pp. 3799-3801.

Zhou, J.J., et al., "Flow conveying and diagnosis with carbon nanotube arrays", Nanotechnology, 2006, vol. 17, pp. 4845-4853.

McKenzie, J.L., et al., "Decreased functions of astrocytes on carbon nanofiber materials", Biomaterials, 2004, vol. 25, pp. 1309-1317.

* cited by examiner

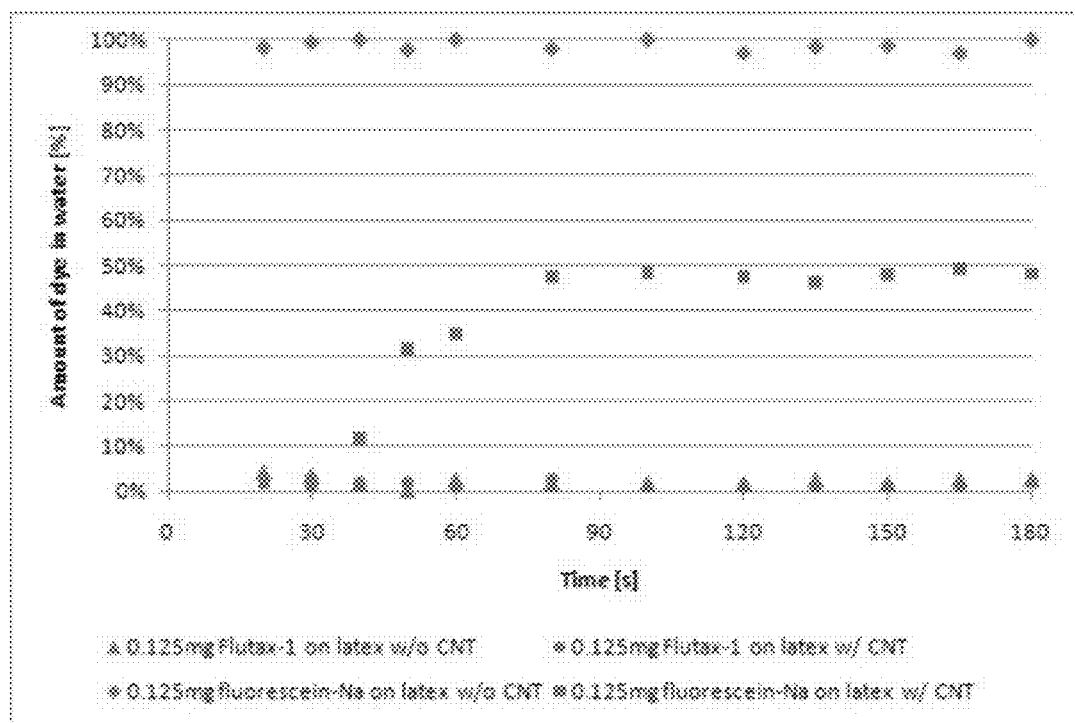

DRUG DELIVERY BY CARBON NANOTUBE ARRAYS

PRIORITY CLAIMS AND CROSS REFERENCE TO RELATED APPLICATIONS

This application claims the benefit of priority from U.S. Provisional Application Ser. No. 61/379,701, filed Sep. 2, 2010, the entire content of which is incorporated herein by reference in its entirety.

TECHNICAL FIELD OF THE INVENTION

The invention generally relates to carbon nanotube based drug delivery methods, devices, and compositions. More particularly, the invention relates to controlled drug delivery using anchored carbon nanotube arrays.

BACKGROUND OF THE INVENTION

Targeted, localized and controlled drug delivery remains a major challenge. In many cases, efficacy of a drug can be improved and the risks of side effects reduced if the therapy is administered locally and/or continuously, rather than through conventional oral ingestion or injection, which produce burst releases. In some cases, dose-limiting toxicity levels are caused by agent losses in vascular travel during transplant procedures. Continuous and accurate local dosing is highly desirable, but remains a major challenge, particularly in the cardiovascular field where requirements for a material's biocompatibility and dosing control are stringent.

Current diffusion-based drug-delivery platforms suffer from very slow mass-transfer process. The published reports indicate involvement of solid/solid diffusion as well as channel (e.g., tubule) and solvent-help (e.g., capillary, osmotic) mechanisms but not convection. (Tepe, et al. 2007 *Touch Briefings* 2007—*Interventional Cardiology*, pp. 61-63; Scheller, et al. 2004 *Circulation* 110:810-814; Diaz, et al. 2005 *J Biol Chem* 280:3928-3937; Creel, et al. 2000 *Circ Res* 86:879-884; Lovich, et al. 2001 *J Pharm Sci* 90:1324-1335; Zilberman, et al. 2008 *J Biomed Mater Res* 84A:313-323; Davies 1997 *N Engl J Med* 336:1312-1314; Arakawa, et al. 2002 *Arterioscler Thromb Vasc Biol* 22:1002-1007; Parekh, et al. 1997 *Gen Pharmac* 29:167-172; Hearn, et al. 2009 *Nature* 458:367-371; Celermajer 2002 *European Heart Journal Supplement F*:F24-F28; Andersen, et al. 2006 *BMC Clinical Pharmacology*, published online 13 Jan. 2006; Oreopoulos, et al. 2009 *J Structural Biology* 168:21-36; Panchagnula, et al. 2004 *J Pharm Sci* 93:2177-2183; Migliavacca, et al. 2007 *Comput Methods Biomech Biomed Engin* 10:63-73; Arifin, et al. 2009 *Pharmaceutical Research*, published online 29 Jul. 2009.) In percutaneous transluminal angioplasty (PCTA) devices, for example, drug washout and overdose remain serious challenges. For oncology applications, for example, localized delivery of sufficient dose of anti-cancer drug via targeted delivery is highly desirable.

In recent years, carbon nanotubes have attracted attention due to their chemical, mechanical and geometric properties. Carbon nanotubes (CNTs) are allotropes of carbon with a cylindrical nanostructure and are members of the fullerene structural family. Nanotubes are categorized as single-walled nanotubes and multi-walled nanotubes. Carbon nanotubes are strong and stiff materials in terms of tensile strength and elastic modulus respectively. Various techniques have been developed to make nanotubes, such as arc discharge, laser ablation, high-pressure carbon monoxide, and chemical vapor deposition.

Researches have been reported on CNT-based drug delivery. For example, a recent study was reported on drug delivery using PEGylated-CNTs. (Liu, et al. 2008 *Cancer Res.* 68: (16), 6652). The reported system is based on covalently attaching drug molecules to PEGylated CNTs. Another research group used carbon nanotube-based tumor-targeted drug delivery system, which consisted of a functionalized CNTs linked to tumor-targeting modules as well as prodrug modules. (Chen, et al. 2008 *J Am Chem Soc* 130:16778-16785.) In both of the afore-mentioned approaches, functionalization of the CNTs is required, which presents a number of complications and procedural drawbacks.

One reported example of angioplasty drug delivery is a PTCA balloon coated with paclitaxel in an iopromide matrix. The balloon is inflated for 30-second contact with vascular wall to allow the matrix to dissolve and paclitaxel to migrate into the smooth muscle cell. (Scheller, et al. 2004 *Circulation* 110:810-814.) Major problems with this device include iopromide being hydrophilic and an X-ray contrast agent. The first causes some drug loss to blood stream (although claimed to be about 6%) and the second leads to adverse reactions for some patients. Furthermore, the balloon still contains about 10% paclitaxel after detachment and only about 15% remains in the plaque.

Another reported example of angioplasty drug delivery is a system using vascular stents made of paclitaxel-eluting composite fibers to deliver about 40% of drug, most of it over 30 days. (Zilberman, et al. 2008 *J Biomed Mater Res* 84A:313-323.) Since the main mass-transfer mechanism of this device is diffusion, the rate is inherently slow. These drawbacks are in addition to the well-documented risks and side effects associated with stents.

For angioplasty drug delivery monitoring, existing technologies typically use a fluorescent dye administered intravenously through a central venous line with a dose adapted to body weight. (Detter, et al. 2007 *Circulation* 116:1007-1014; Hattori, et al. 2009 *Circ Cardiovasc Imaging* 2:277-278; Hosono, et al. 2010 *Interact CardioVasc Thorac Surg* 10:476-477; Tanaka, et al. 2009 *J Thorac Cardiovasc Surg* 138:133-140; Waseda, et al. 2009 *JACC Cardiovascular Imaging* 2:604-612.) The illumination is provided by near-infrared laser diodes with a typical output of 80 mW in a field of view of 10 cm in diameter, eliminating tissue warming and eye protection concerns. The fluorescence emission of the excited dye is typically detected by an IR-CCD camera and digitized with a frame grabber that provides real-time recording.

Therefore, there remains an urgent and unmet need for improved drug delivery systems addressing the above-mentioned shortcomings, particularly in the field of angioplasty drug delivery.

SUMMARY OF THE INVENTION

The invention is based, in part, on the unique approach to drug delivery using anchored carbon nanotube arrays. In particular, the invention provides targeted, localized, and controlled drug delivery using novel anchored carbon nanotube arrays that carry (e.g., non-covalently) the agent to be delivered, including therapeutic and diagnostic agents.

In one aspect, the invention generally relates a method for delivering an agent to a patient in situ. The method includes: (a) providing a plurality of carbon nanotubes; (b) depositing the agent to the plurality of carbon nanotubes such that the agent is non-covalently associated with the plurality of carbon nanotubes; (c) placing the plurality of carbon nanotubes deposited with the agent at a target location in the patient's body; and (d) allowing the agent to diffuse from the plurality of carbon nanotubes, thereby delivering the agent in situ.

In another aspect, the invention generally relates to an implantable drug delivery device. The implantable drug delivery device includes: (a) an implantable device; (b) an array of carbon nanotubes anchored on the implantable drug delivery device; and (c) an agent deposited on the array of carbon nanotubes, wherein the agent is not covalently bound to the carbon nanotubes.

In yet another aspect, the invention generally relates to a method for monitoring in situ delivery of an agent. The method includes: (a) providing a plurality of carbon nanotubes non-covalently associated thereon a pharmaceutical agent and a second agent capable of exhibiting a spatially detectable signal; (b) placing the plurality of carbon nanotubes at a target location in the patient's body; and (c) measuring the detectable signal exhibited from the second agent to monitor the deliver of the pharmaceutical agent in situ.

The invention disclosed herein enables improved devices, methods and compositions for treating a number of conditions where targeted, localized, and controlled drug delivery are required.

BRIEF DESCRIPTION OF THE DRAWINGS

FIG. 1 shows an exemplary angioplasty-balloon fitted with carbon nanotubes.

FIG. 2 shows an exemplary carbon nanotube array prepared via capillography methods.

FIG. 3 shows schematics of an array of anchored carbon nanotubes (as tall as 1 mm) on a flexible substrate. (Sansom, et al. 2008 *Nanotechnology* 19:035302; Sansom 2007 Ph.D. Thesis, California Institute of Technology; Noca, et al. U.S. Pat. No. 7,491,628; Huang, et al. 2007 *Nanotechnology* 18:305301; Gharib, et al. U.S. Pat. App. 20080145616A1.)

FIG. 4 shows exemplary surface-to-volume ratio comparisons of bundled anchored CNTs and conventional microneedles. For the same total needle diameter of 50 μm, a bundle of ACNT has almost 100 times larger surface area than a conventional microneedle, assuming a modest CNT spacing of 100 nm center-to-center. The uppermost line represents the surface-to-volume gain by decreasing the CNT spacing by a factor of 2.

FIG. 5 shows a schematic drawing of anchored CNTs (as tall as 1 mm) with drugs deposited in its interstices. (Zhou, et al. 2006 *Nanotechnology* 17:4845-4853.)

FIG. 6 shows a flutax-coated anchored CNT array (a, top) and an uncoated CNT array (b, bottom).

FIG. 7 shows: (a, top) Exemplary results of recovered fluorescein sodium and flutax-1 with the same initial concentration in DI water. (b, bottom) Exemplary results of recovered fluorescein sodium with various initial concentrations in DI water.

FIG. 8 shows exemplary results from rubbing experiment using 3×1×5/128-inch glass microscopy slide rubbed on substrates made of CNT-fitted latex sheet (left) and bare latex sheet (right).

FIG. 9 shows exemplary images of 3×1×5/128-inch glass microscopy slides used in rubbing experiment. A significant amount of flutax-1 has been washed-out from the substrate made of bare latex sheet (a, top) and almost no flutax-1 are washed-out from substrate made of CNT-fitted latex sheet (b, bottom).

FIG. 10 shows exemplary recovered flutax-1 in pure ethanol after the rubbing experiment, where the bare latex sheet shows that no more flutax-1 remains (left) while much flutax-1 still remains on the CNT-fitted latex sheet (right); tubes OD=16 mm.

FIG. 11 shows an exemplary PET angioplasty balloon without CNTs (a, top) and a CNT-partially-fitted PET angioplasty balloon (b, bottom). The black region on the CNT-partially-fitted PET angioplasty balloon is an array of vertically aligned CNTs anchored on latex, which cover the outer surface of the PET balloon.

FIG. 12 shows an exemplary experiment setup using agar gel inside a 860-μm-ID, 1,450-μm-OD glass capillary tube with a substrate made of CNT-fitted latex sheet (left) and bare latex sheet (right).

FIG. 13 shows an exemplary series of time lapse images of mass transfer in 5 weight % agar gel, where the flutax-1 were transferred via ~300 μm CNT-fitted latex sheet (left) and a bare latex sheet (right).

FIG. 14 shows an exemplary mass transfer profile of flutax-1 in 5 weight % agar gel, where the flutax-1 was transferred via ~300 μm CNTs-fitted latex sheet (left) and a bare latex sheet (right).

FIG. 15 shows: (a) Location of 1% concentration vs. time for a dried flutax-1 positioned as a shallow flat layer (squares, smooth line) and within an anchored CNT array (triangles, dashed line). The squares and triangles mark experimental data and the dashed and smooth lines are numerical solutions of the appropriate model. Schematic geometric descriptions of the problem for a thin flutax layer and CNT array are presented in (b) and (c), respectively.

DETAILED DESCRIPTION OF THE INVENTION

The invention is based in part on the discovery of a universal drug-carrying and delivery platform capable of delivering targeted, localized, and controlled amounts of drugs to a target location within a patient's body. The devices, systems, methods and compositions of the invention significantly remedy the difficult dose control problems in current PCTA devices as well as the complexity and costs associated with CNT functionalizations. Different from the common methods that have been published earlier (e.g., Tepe, et al. 2007 *Touch Briefings* 2007—*Interventional Cardiology*, pp. 61-63; Scheller, et al. 2004 *Circulation* 110:810-814; Diaz, et al. 2005 *J Biol Chem* 280:3928-3937; Creel, et al. 2000 *Circ Res* 86:879-884), the device of the invention incorporates a drug on CNTs without having to functionalize the CNTs. Conjugating drugs with functionalized CNTs is inherently complicated and expensive. Additionally, the functionalizing process renders the CNTs hydrophilic, such that the drug attached to the CNTs is vulnerable to washout by the blood stream. Additionally, as disclosed herein, the ability to penetrate the arterial plaque cap and to deliver the drugs directly to the inner part of the plaque is a major advantage of a CNT-fitted angioplasty balloon over the conventional angioplasty-balloon or stent-fitted angioplasty balloon.

CNTs, since their discovery, have been studied for various applications ranging from highly adhesive layers, heat sinks, structural composites, vibration damping layers, lithium storages, to field emitters, due to their exceptional properties. (Iijima 1991 *Nature* 354: 56-58; Yurdumakan, et al. 2005 *Chem Commun* 30:3799-3801; Xu, et al. 2004 *IEEE Inter Society Conference on Thermal Phenomena* 29:549-555; Veedu, et al. 2006 *Nature Materials* 5:457-462; Daraio, et al. 2004 *Appl Phys Lett* 85:5724-5726; Wang, et al. 2006 *Metals and Materials Int'l* 12:413-416; Manohara, et al. 2005 *J Vac Sci Tech B*23:157-161.) The strength and flexibility of CNTs are just two of many exceptional physical properties of CNTs.

The accepted Young's elastic modulus for individual CNTs is extraordinarily high, approaching 1 TPa (somewhat less for multi-walled CNTs than single-walled CNTs), which is almost 5 times higher than stainless steel. (Wong, et al. 1997 *Science* 277:1971-1975, Krishnan, et al. 1998 *Phys Rev B* 58: 14013-14019.)

This high Young's modulus of elasticity allows the anchored CNTs to penetrate soft surfaces such as biological tissues upon touching and consequently have the potential of delivering drugs directly to the inner part of the tissue. According to the linear elastic beam theory, the critical force for buckling of an axially loaded clamped cylindrical beam in compression can be calculated by:

$$F_{crit} = \frac{\pi^3 E d^4}{256 L^2}$$

where d is the diameter of the beam, L is the length, and E is the Young's modulus. Assuming a bundle of several CNTs is clamped together on the substrate, and typical diameter and length of a bundle of CNTs are 1 μm and 500 μm, respectively, the critical buckling force for each bundle of CNTs is around 0.484 μN, or equivalent to 617 kPa. This critical buckling force for each bundle of CNTs is great enough to overcome the required fracture stress of the arterial plaque cap, for example, about 254.8 kPa. (Holzapfel, et al. 2004 *J Bio Eng* 126:657-665.) As it is demonstrated herein, CNT bundles anchored on a flexible substrate are sufficiently strong to penetrate soft tissues, e.g. arterial wall or arterial plaque cap, when pressed upon and can deliver a drug directly to the inner part of these targets.

Another extraordinary property of CNTs that makes them a great fit for drug delivery is the hydrophobicity of CNTs. By placing the drugs in the interstices of an array of CNTs, the highly hydrophobic CNTs protect the drugs from being washed out by any aqueous solution. Therefore, the CNT-fitted angioplasty balloon, for example, would protect the drugs from being washed-out during vascular travel to the target location.

Thus, in one aspect, the invention generally relates a method for delivering an agent to a patient in situ. The method includes: (a) providing a plurality of carbon nanotubes; (b) depositing the agent to the plurality of carbon nanotubes such that the agent is non-covalently associated with the plurality of carbon nanotubes; (c) placing the plurality of carbon nanotubes deposited with the agent at a target location in the patient's body; and (d) allowing the agent to diffuse from the plurality of carbon nanotubes, thereby delivering the agent in situ.

In another aspect, the invention generally relates to an implantable drug delivery device. The implantable drug delivery device includes: (a) an implantable device; (b) an array of carbon nanotubes anchored on the implantable device; and (c) an agent deposited on the array of carbon nanotubes, wherein the agent is not covalently bound to the carbon nanotubes.

In yet another aspect, the invention generally relates to a method for monitoring in situ delivery of an agent. The method includes: (a) providing a plurality of carbon nanotubes non-covalently associated thereon a pharmaceutical agent and a second agent capable of exhibiting a spatially detectable signal; (b) placing the plurality of carbon nanotubes at a target location in the patient's body; and (c) measuring the detectable signal exhibited from the second agent to monitor the deliver of the pharmaceutical agent in situ.

In certain embodiments, the agent is a pharmaceutical agent capable of providing a therapeutic effect on the patient. Exemplary pharmaceutical agents include: adrenaline (epinephrine) amphetamine, atropine taxol (or its fluorescent derivative flutax-1) and statins.

In certain other embodiments, the agent is a diagnostic agent capable of providing a detectable signal or image indicating a biologically relevant state of the subject. Exemplary diagnostic agents include: electrochemical detectors of chemical warfare agents, utilizing superior electrical properties of carbon nanotubes.

In certain preferred embodiments, the agent comprises an aromatic moiety (e.g., arenes and heteroarenes). The aromatic moiety may include one or more heteroatoms selected from N, O and S. The aromatic moiety may include a single aromatic ring or two or more independent or fused rings. The agent may be mono-aromatic or multi-aromatic.

In certain embodiments, the agent comprises a non-aromatic extended π-bond system.

Preferably, the agent may have a molecular weight from about 130 to about 1500 (e.g., from about 130 to about 1200, from about 130 to about 1000, from about 200 to about 1500, from about 200 to about 1200, from about 200 to about 1000, from about 500 to about 1000).

In certain preferred embodiments, the plurality of carbon nanotubes are in an array format and anchored on an implantable device. In certain preferred embodiments, the plurality of carbon nanotubes are not surface functionalized, e.g., for covalent attachment.

In certain preferred embodiments, the implantable device is an angioplasty balloon.

Figure 1B:
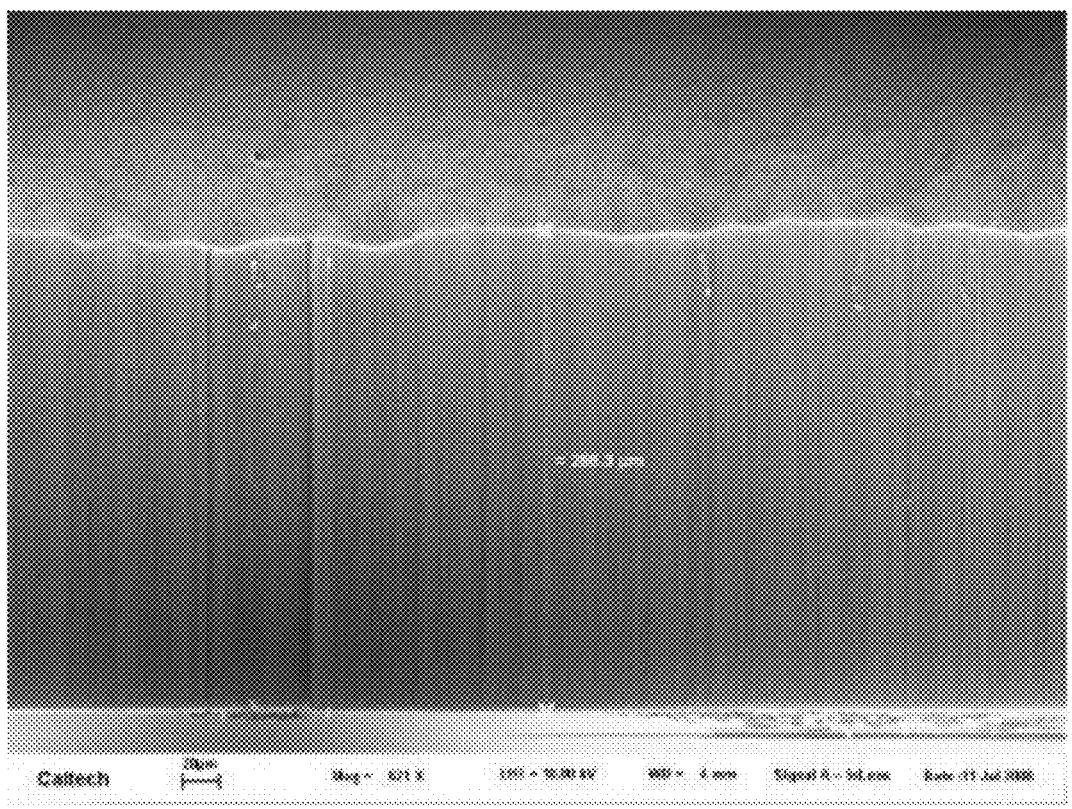
Figure 1C:
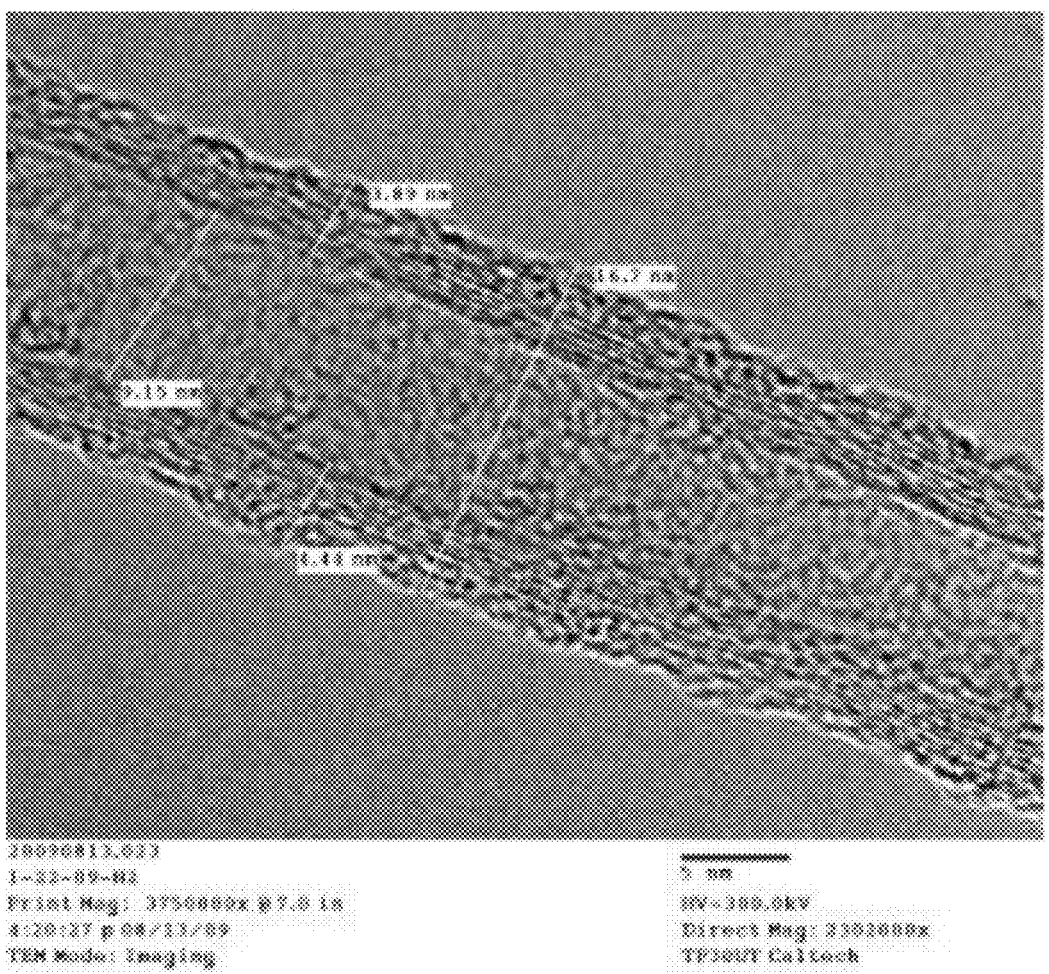

The angioplasty balloon is preferably anchored uniformly with the plurality of carbon nanotubes, e.g., without surface functionalization. The density of the plurality of carbon nanotubes is typically from about $10^{10}$ nanotubes/cm$^2$ to about $10^{11}$ nanotubes/cm$^2$ (e.g., about $2 \times 10^{10}$ nanotubes/cm$^2$, $4 \times 10^{10}$ nanotubes/cm$^2$, $6 \times 10^{10}$ nanotubes/cm$^2$, $8 \times 10^{10}$ nanotubes/cm$^2$.) (FIG. 1.)

In a preferred embodiment, the agent is an agent for treating arterial plaque and the target location is interior wall of a vascular lumen of the patient. In some embodiments, the target location is inside an arterial plaque whereby at least some of the carbon nanotubes penetrate the outer lining and enter the interior of an arterial plaque.

The carbon nanotubes may be prepared by any suitable means, e.g., by thermal chemical vapor deposition. In some embodiments, the carbon nanotubes are multi-walled. In some embodiments, the carbon nanotubes are single-walled. The desired specifications of carbon nanotubes are dependent on the applications including the requisite strength of the nanotubes.

In certain embodiments, the agent is deposited to the carbon nanotubes by a method that includes: mixing the agent in a low surface tension solvent forming a solution of the agent; coating the plurality of carbon nanotubes with the solution of the agent; and drying the coated plurality of carbon nanotubes, thereby removing the solvent while leaving the agent associated with the plurality of carbon nanotubes.

The low surface tension solvent may be any suitable solvent, for example, an alcohol. In certain preferred embodiments, the low surface tension solvent is pure (200 proof) ethanol or another water-free alcohol.

The drug load is determined according to the requirements of the application. Drug load may range from about 0.1 mg to about 20 mg (e.g., from about 0.1 mg to about 10 mg, from about 0.1 mg to about 5 mg, from about 0.1 mg to about 2.5 mg, from about 1.0 mg to about 20 mg, from about 1.0 mg to about 10 mg.)

CNTs can be formed in several ways, a simple way being a CVD method with a catalyst-coated substrate (typically a few nanometers of iron coated onto silicon wafer) prepared in advance and placed in a tube furnace under saturated flow of carbon containing feed-gas (e.g., ethylene) small portion of reducer feed-gas, e.g. hydrogen, and elevated to proper temperature (e.g., 725° C.). Thermal CVD growth of CNTs in this way generates vertically aligned CNTs on the growth substrate. (Sansom, et al. 2008 *Nanotechnology* 19:035302; Sansom 2007 *Experimental Investigation on Patterning of Anchored and Unanchored Aligned Carbon Nanotube Mats by Fluid Immersion and Evaporation*, Ph.D. Thesis, California Institute of Technology.)

Various methods and techniques have been developed that allow the preparation of anchored CNTs, including microscale fluid transport and control techniques by "nanowicking" and by self-assembly pattern formation and a method for controllable anchoring of CNTs within polymer layers (Sansom, et al. 2008 *Nanotechnology* 19:035302; Sansom 2007 *Experimental Investigation on Patterning of Anchored and Unanchored Aligned Carbon Nanotube Mats by Fluid Immersion and Evaporation*, Ph.D. Thesis, California Institute of Technology; Zhou, et al. 2006 *Nanotechnology* 17:4845-4853; U.S. Pat. No. 7,491,628 Noca, et al.; Huang, et al. 2007 *Nanotechnology* 18:305301; U.S. Pat. App. 20080145616A1 by Gharib, et al.). Tall CNT arrays have been grown in arbitrary patterns (e.g., bundles, rows, geometric shapes) on a substrate with heights of over 1 mm. (Broni-kowski 2007 *J Phys Chem C* 111:17705-17712.)

In contrast to the length of CNTs that can be varied relatively easily by varying either the thickness of catalyst layer or the growth time, the packing density of an array of CNTs is relatively harder to vary. One way to adjust the packing density of the CNTs is by changing the timing and duration of the hydrogen exposure during the CNT growth. (Nessim, et al. 2008 *Nano Lett* 8:3587-3593.) By this method, the packing density of as-grown CNTs can be varied from $3.9 \times 10^9$ to $4.9 \times 10^{10}$ CNTs/cm². Another approach is by compressing the as-grown CNTs by external mechanical force or capillary force. (Wardle, et al. 2008 *Adv Mater* 20:2707-2714; Futaba, et al. 2006 *Nature Material* 5:987-994). By using an external mechanical force to compact the as-grown CNTs, the packing density of CNTs can be increased up to about 20%. By using a capillary force to collapse a pack of CNTs, the packing density of CNTs can be increased up to about 50%, or equivalent to the increase of packing density from $4.3 \times 10^{11}$ to $8.3 \times 10^{12}$ CNTs/cm².

Figure 2:
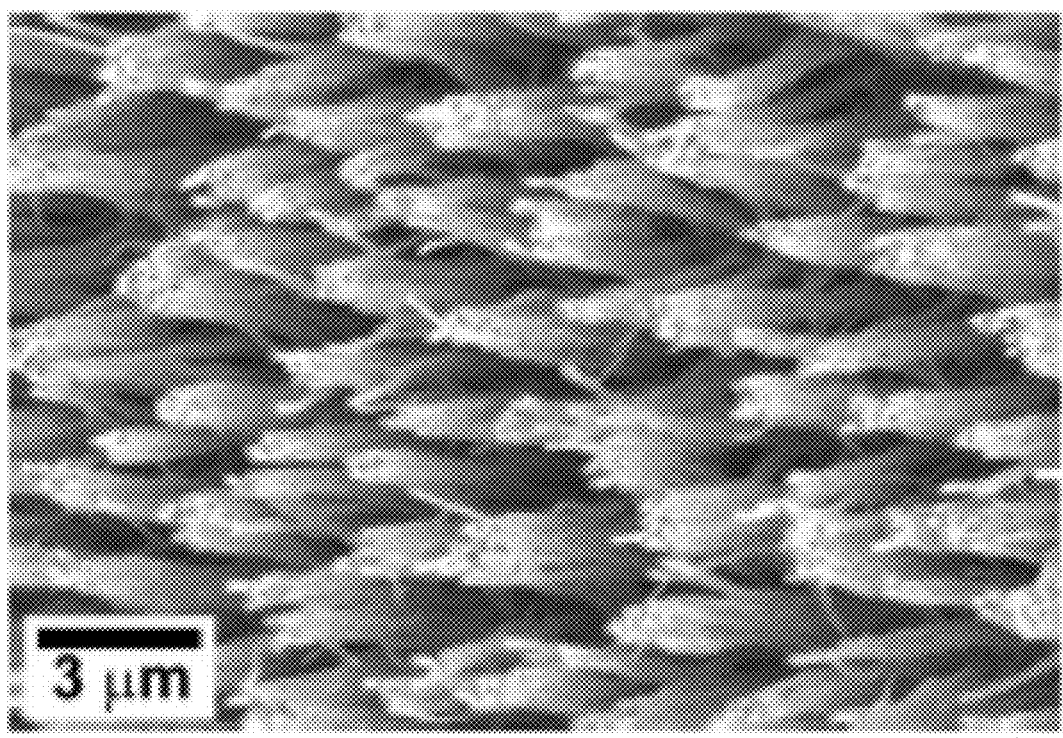

A major challenge for the vertically aligned CNTs is the poor adhesion of the CNTs to their growth substrates, e.g., silicon wafer. Although the mechanical properties of individual CNTs are excellent, the collective properties of bulk vertically-aligned CNTs have not been as good as expected, because of the weak bond between the base of the CNTs and their growth substrates. A method has been developed to overcome this problem by anchoring the CNTs in a layer of flexible polymeric materials, e.g., PDMS (polydimethylsiloxane), PMMA (poly(methyl methacrylate)), or latex. (Sansom, et al. 2008 *Nanotechnology* 19:035302.) As-grown CNTs are manipulated by handling their growth substrate, inverted into a spin-coated polymer layer, and the assembly is cured (usually by heat). (FIG. 2).

The CNT's growth substrate may then be removed. The CNT-growth can be patterned by controlling the patterning of the thin iron catalyst layer prior to the CNT-growth step. Through separate control of polymer layer thickness and CNTs length, the depth of anchoring of the CNTs into the flexible polymer layer can be controlled. Thus, any pattern of as-grown CNTs, defined by catalyst pattern may be inverted and anchored into a polymer layer as required.

CNTs anchored in PDMS can withstand the shear stress up to 230 dyne/cm² and tensile stress up to 64.5 kPa. (Sansom, et al. 2008 *Nanotechnology* 19:035302). The effective adhesion strength between the CNTs and the flexible polymeric layer depends on the depth of anchoring of the CNTs into the polymer layer, the strength of the bond between CNTs and the polymer layer, and the fracture toughness of the polymeric layer.

Anchored CNTs on a flexible polymeric layer can be designed and prepared such that they have the requisite mechanical strength ensuring that no CNTs would enter the blood circulation or be left in the living tissues that may pose harm to the patient. The biocompatibility of CNTs has been demonstrated, including evidences that show various types of living cells (e.g. neuronal cells, osteoblast cells and fibroblast cells) can be supported by CNTs (Hu, et al. 2004 *Nano Lett* 4:507-511; McKenzie, et al. 2004 *Biomaterials* 25:1309-1317; Webster, et al. 2004 *Nanotech* 15:48-54; Gabay, et al. 2005 *Physica A* 350:611-621; Price, et al. 2003 *Biomaterials* 24:1877-1887; Elias, et al. 2002 *Biomaterials* 23:3279-3287; Correa-Duarte, et al. 2004 *Nano Lett* 4:2233-2236.) Some studies have been reported that CNTs may present certain health problems, especially related to lung toxicity, cytotoxicity, and skin irritation. (Huczko, et al. 2001 *Fullerene Sci Tech* 9:247-250; Huczko, et al. 2001 *Fullerene Sci Tech* 9:251-254; Huczko, et al. 2005 *Fullerenes Nanotubes Carbon Nanostruct* 13:141-145; Lam, et al. 2004 *Toxicol Sci* 77:126-134; Warheit, et al. 2004 *Toxicol Sci* 77:117-125; Muller, et al. 2005 *Toxicol App Pharmacol* 207:221-231; Shvedova, et al. 2003 *J Toxicol Environ Health A* 66:1909-1926; Monteiro-Riviere, et al. 2005 *Toxicol Lett* 155:377-384; Jia, et al. 2005 *Environ Sci Technol* 39:1378-1383; Cui, et al. 2005 *Toxicol Lett* 155:73-85; Tamura, et al. 2004 *Key Eng Mater* 254-6:919-922.) Thus, to minimize the risk of side effects, the minimum mechanical strength of the ACNT on a CNTs-fitted drug delivery system must be sufficiently higher than the maximum shear stress induced by the tissue.

Figure 3:
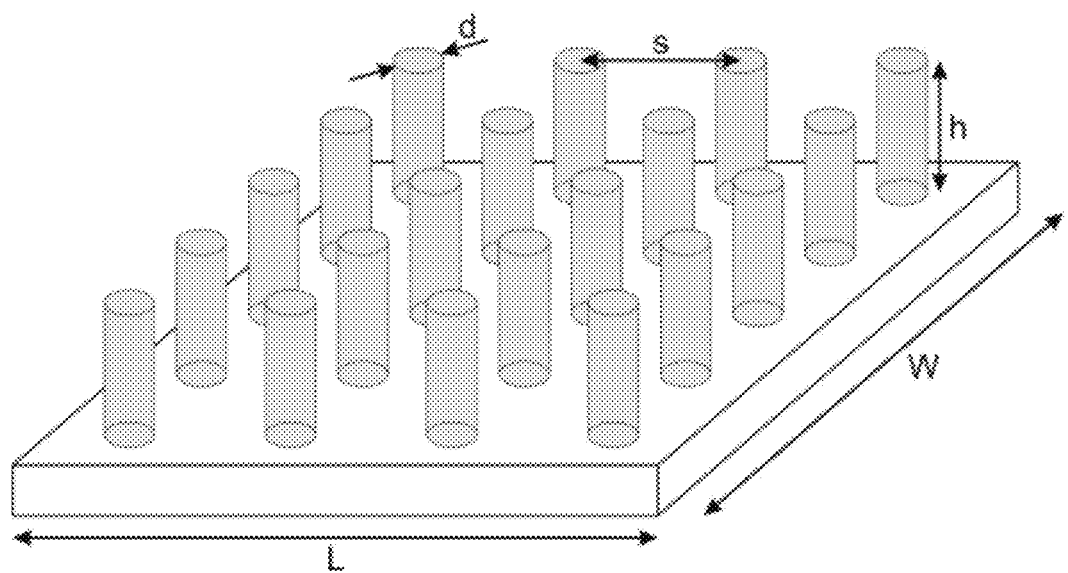

Diffusion is an important mechanism in delivering drugs from any pharmaceutical system. The release kinetics of a drug delivery system depends on the initial concentration of the drug and the surface area of the system. Therefore, to improve the drug delivery mechanism, it is crucial for a system to have a sufficiently large surface area. Such a system can essentially be made by fitting an array of anchored CNT arrays onto a flexible substrate (FIG. 3).

The following expression compares the surface area of a CNT-fitted flexible substrate with a bare flexible substrate without CNT-enhancement.

$$\frac{A_{CNT\text{-}fitted\text{-}substrate}}{A_{bare\text{-}substrate}} = \frac{\frac{2\sqrt{3}\,\pi d h W L}{3s^2}}{WL} = \frac{2\sqrt{3}\,\pi d h}{3s^2}$$

Where d is the diameter of individual CNTs, h is the length of individual CNTs, s is the distance between individual CNT, W and L are the width and length of the flexible substrate respectively. Using the following assumed typical values, where d=10 nm, s=100 nm and h=500 μm, the following result is obtained:

$$\frac{A_{CNT\text{-}fitted\text{-}substrate}}{A_{bare\text{-}substrate}} = 1813.17$$

This indicates that for a CNT-fitted drug delivery platform, the mass-transfer surface for delivering drugs is about 1,800 times greater than that of a non-CNT-fitted platform of similar geometry. Therefore, there is a substantial increase in drug mass transfer rate when a drug delivery platform is fitted with CNTs.

Figure 4:
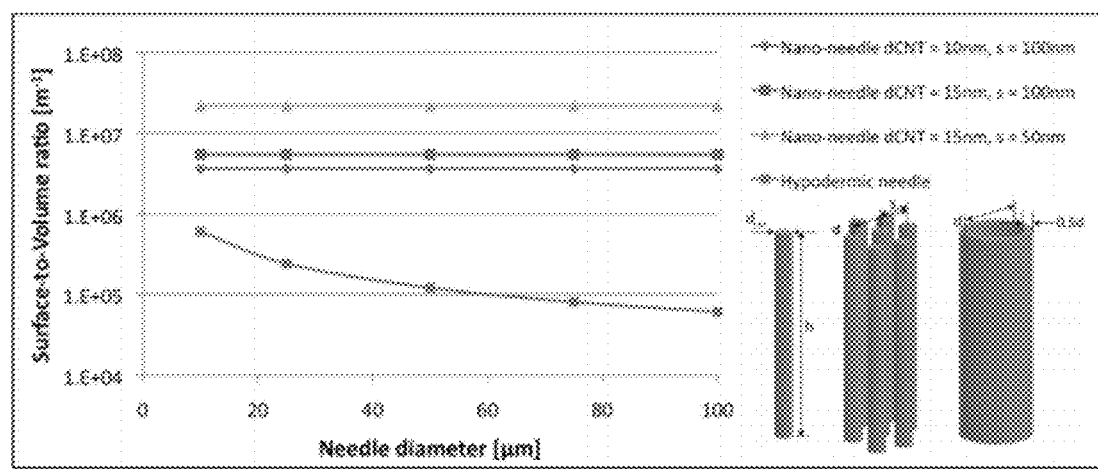

Compared to a simple hollow microneedle, the surface-to-volume ratio of an anchored CNT bundle is at least one order of magnitude greater (FIG. 4). This is again crucial for a local drug delivery platform. This large surface-to-volume ratio also shows that a high dose of drugs can be placed in a small size of CNT-fitted drug delivery platform.

Figure 5:
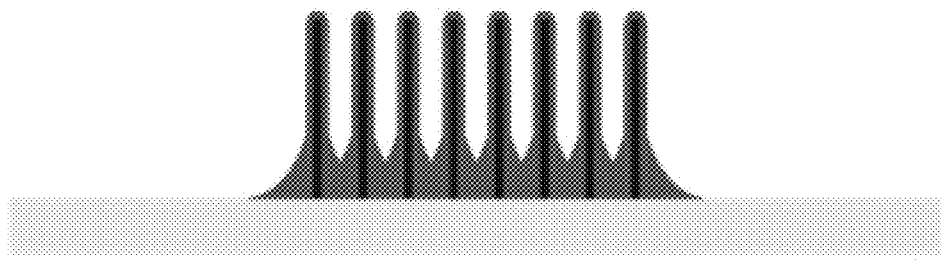
Figure 6A:
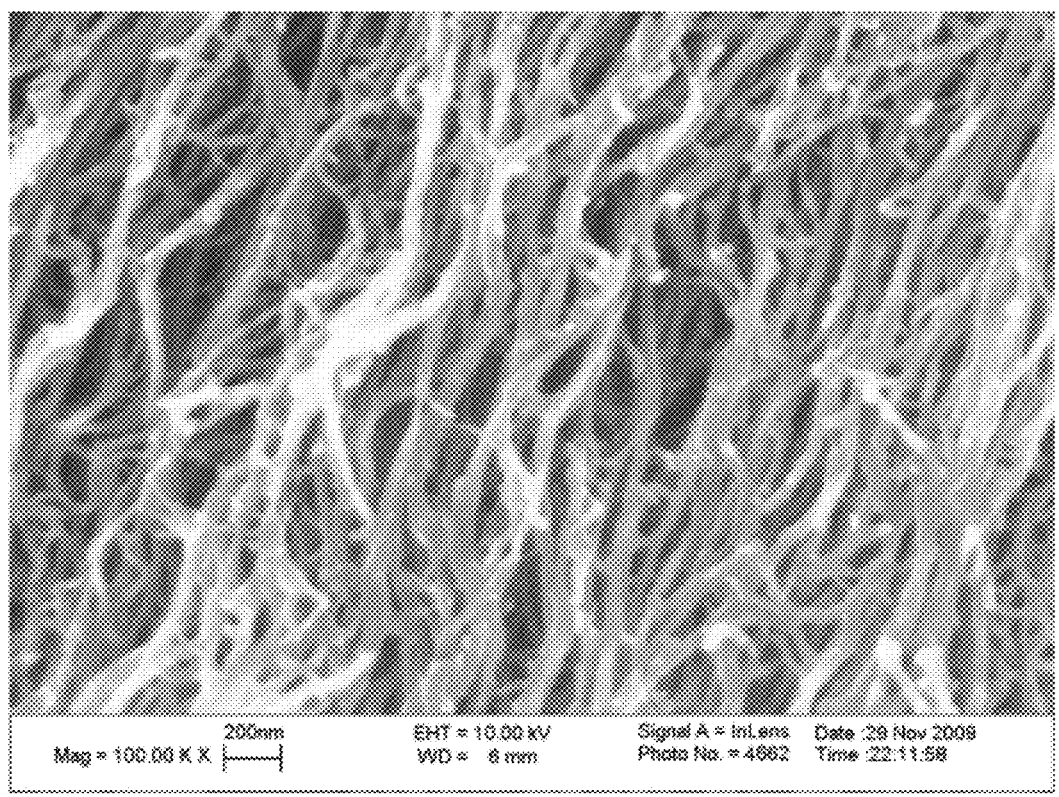
Figure 6B:
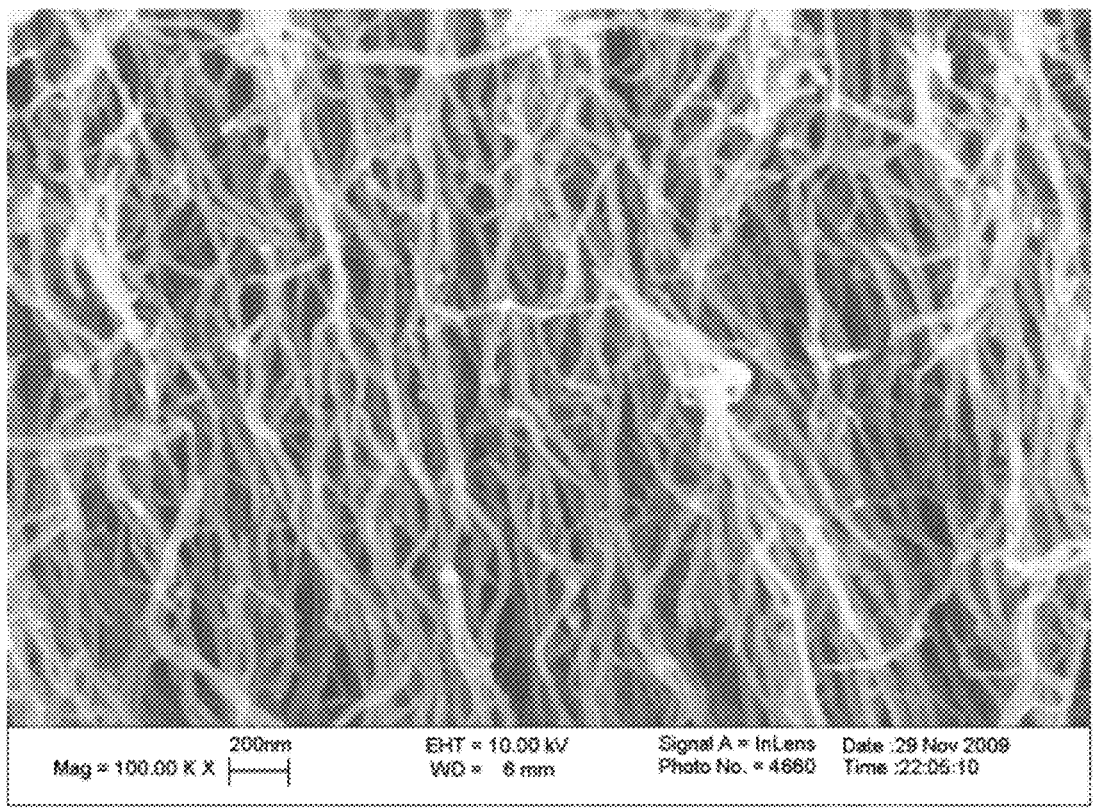

The drug depositing technique for depositing drugs to CNTs may be any suitable method. A novel approach disclosed here is to use a very low surface tension liquid (e.g., substantially lower than 72 dyne/cm (water, 25° Celsius), such as isopropanol, ethanol and acetone) to place the drugs on the CNTs. Fluid transport based on wicking through a nano-fibrous material has been previously studied and characterized. (Zhou, et al. 2006 Nanotechnology 17:4845-4853.) The same phenomenon is employed here for depositing the drugs in the interstices of the anchored CNT array from their solutions followed by thorough drying (FIG. 5). Using this technique, anchored CNTs were coated with both flutax-1 and uranine (sodium salt of fluorescein) (FIG. 6).

The drug depositing technique disclosed herein is a straightforward and less expensive method to place drugs within an anchored CNT array. Using this method, drugs can be placed in an anchored CNT array without having the need to functionalize the surface of the CNTs. Generally speaking, this method works preferably for drugs that have one or more aromatic moieties and/or extended π-bond systems such as atropine and amphetamine, which help with the creation π-π interactions with the CNTs. By creating strong π-π interactions, the need to functionalize the CNT beforehand is eliminated. Reduced surface tension liquids (optionally having a surfactant such as sodium dodecyl sulfate (SDS) and similar detergents) easily wicked through CNT arrays. For example, a device can be deposited with the drugs in the interstices of CNTS using an ethanol solution of the drug followed by thorough drying to remove the solvent.

By attaching a fluorescent molecule to the drug, e.g., taxol, direct photographic observation and monitoring of its movement into plaque can be accomplished, for example, using fiber-optic-based technology and calibration methods. (U.S. Pat. No. 5,116,317 by Carson, et al.; U.S. Pat. No. 4,842,390 by Sottini, et al.; Tepe, et al. 2007 *Touch Briefings* 2007 —*Interventional Cardiology*, pp. 61-63; Scheller, et al. 2004 *Circulation* 110:810-814.) Substantial increases in drug mass transfer rate can be achieved when the angioplasty balloon is fitted with anchored CNTs, as disclosed herein.

In one embodiment, flutax-1 (i.e., a conjugated paclitaxel and fluorescein) is used. (Diaz, et al. 2005 *J Biol Chem* 280:3928-3937; Creel, et al. 2000 *Circ Res* 86:879-884; Lovich, et al. 2001 *J Pharm Sci* 90:1324-1335.) Using flutax-1 allows measurement of paclitaxel delivery to an arterial-plaque, optically and directly. This eliminates the need for currently popular high-performance liquid chromatography (HPLC) approach that would need biopsy, or for $^3$H radio-labeled paclitaxel measurement. (Creel, et al. 2000 *Circ Res* 86:879-884.) Fabrication of this device is translatable to industrially scalable processes like roll-to-roll manufacturing for combining CNTs on substrates and polymer layers that allows for very low-cost production.

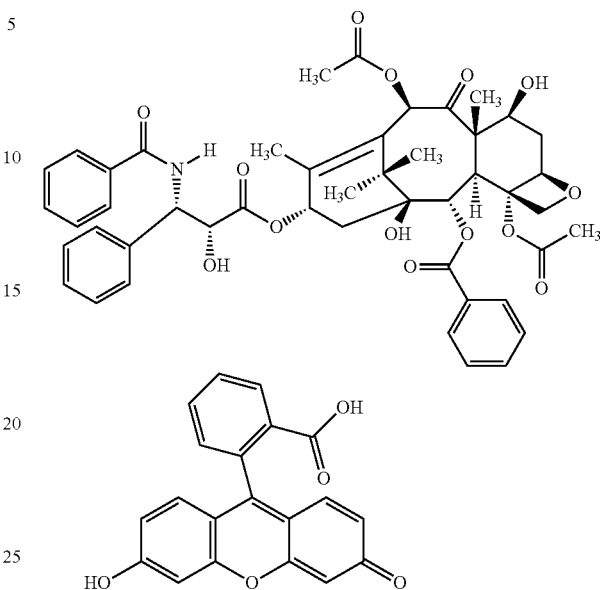

Molecular Structures of Paclitaxel (Left) and Fluorescein (Right)

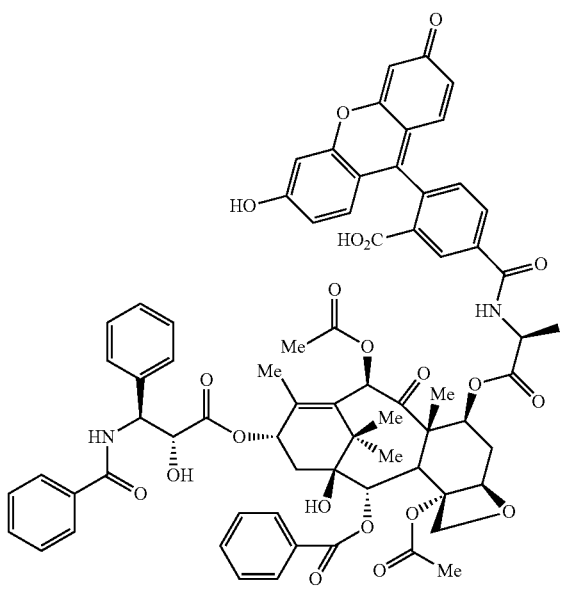

Molecular Structure of Flutax-1, a Conjugated Paclitaxel/Fluorescein

The studies disclosed herein include micromechanics and nano-dynamics relevant to insertion mechanism of nano-structures into model tissues and directly-on-target interstitial mass-transfer phenomena involved with such insertion. The ability to penetrate the arterial plaque cap and deliver the drugs directly inside the plaque is clearly an outstanding advantage of a CNT-fitted angioplasty balloon over the conventional angioplasty-balloon or stent-fitted angioplasty balloon.

Other studies disclosed herein relate to the prevention of the carried drugs from being rubbed-out/washed-away during procedure/travel to the target location. It is important to note that, due to the hydrophobic nature of CNTs, aqueous media such as blood plasma do not easily reach the interior spaces of the CNTs where the drug is deposited. By minimizing drug loss, the risks of overdosing patients may be reduced considerably, another outstanding advantage of an anchored CNT-fitted angioplasty over other drug-delivery devices. Studies and results disclosed herein provide critical information needed for fabricating specific-target drug delivery platforms and for guiding the development of novel drug delivery systems requiring access to interstitial spaces.

Drugs protection experiments were conducted to show that the CNTs protect the deposited drugs from being washed away by blood-like liquids. Two types of dyes were used in these experiments, the fluorescein sodium that represents the hydrophilic drugs and flutax-1 that represents the hydrophobic drugs. Two types of specimens were used, a bare sheet of latex and a sheet of latex with CNTs anchored on one side. Since the CNTs are highly hydrophobic, both fluorescein sodium and flutax-1 were dissolved in ethanol so that both dyes could go into the interstices of the CNTs. The same amounts of both fluorescein sodium and flutax-1 were put in each specimen and allowed to dry. After the dye dried, each specimen was placed in 2 mL of DI water (to simulate blood) and the concentration of the dye was analyzed using spectrophotometer.

Figure 7B:
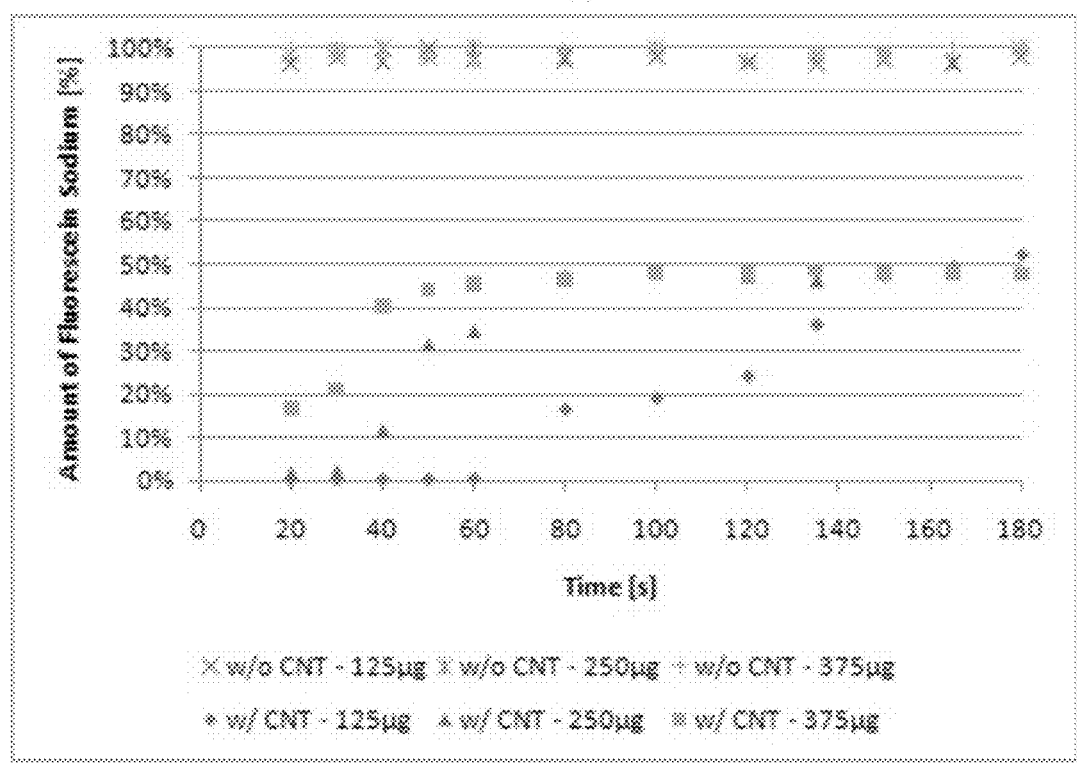

The results showed that the hydrophobicity of CNTs protected the deposited drugs, which could not be easily washed out by DI water. On the contrary, the DI water was able to wash out the fluorescein sodium easily (FIG. 7, top). Notice the obvious difference of the recovered amount of fluorescein sodium between the bare latex samples and the CNT-fitted latex samples. The bare latex samples lost almost all of their initial concentration of fluorescein sodium, while the CNT-fitted latex samples retained about 50% of their initial concentration of the fluorescein sodium.

Another set of experiments was done using various concentrations of fluorescein sodium on both types of specimens (FIG. 7, bottom). The time to wash out the fluorescein sodium in DI water for the CNT-fitted latex samples depended on the initial concentration. Lower initial concentration lead to longer time that was needed to wash out the fluorescein sodium. This was not observed with the bare latex samples. The bare latex samples could not retain the fluorescein sodium from being washed away by DI water for whatever the initial concentration was.

Figure 8:
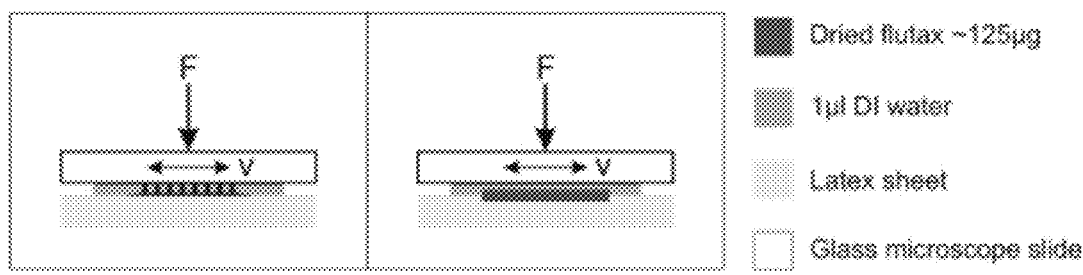
Figure 9A:
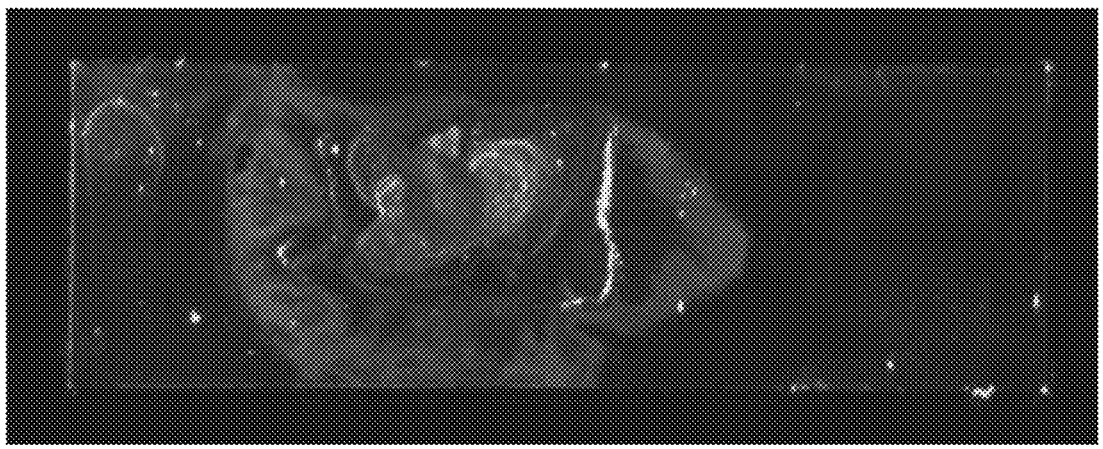
Figure 9B:
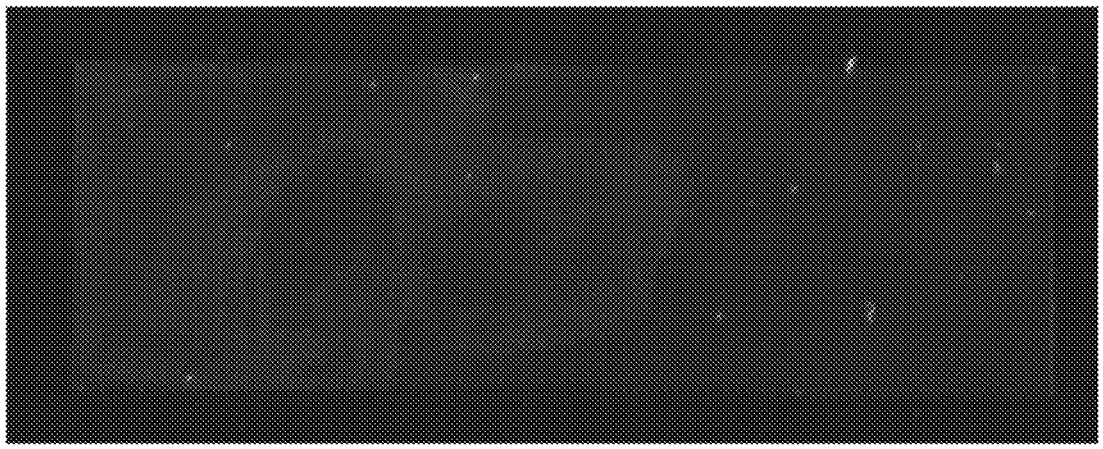
Figure 10:
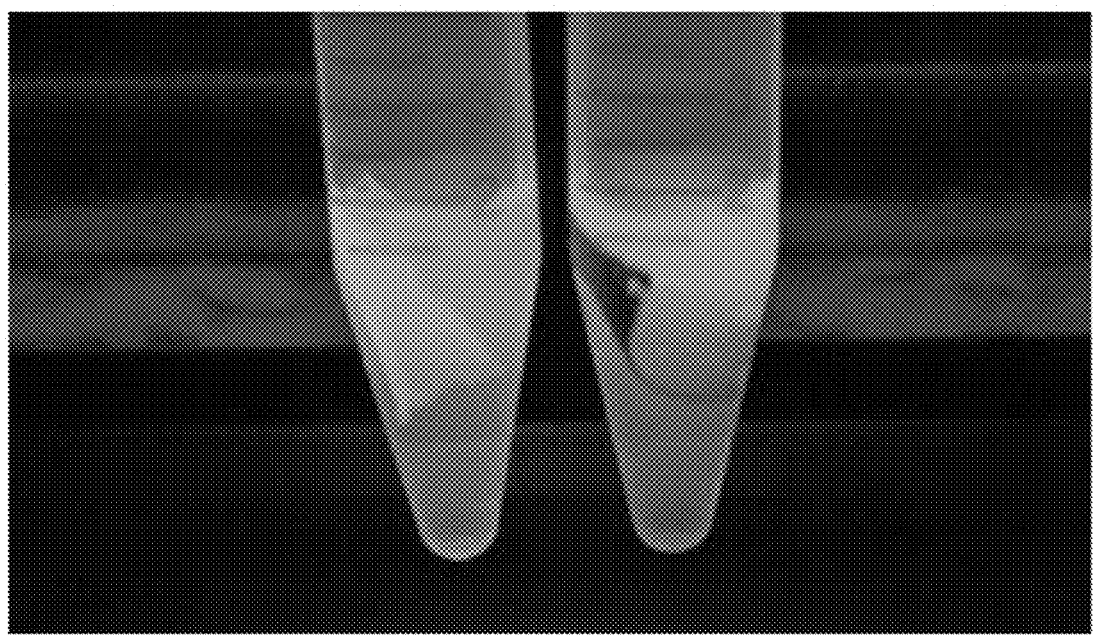

Another experiment was performed that targeted possible drug removal from CNT-fitted drug delivery platform by mechanical (e.g., rubbing) actions during its cardiovascular travel. Two types of specimens were used, a bare sheet of latex and a sheet of latex with CNTs anchored on one side. On each specimen, approximately 125 µg of flutax-1 was deposited by successively dropping small volumes of its ethanol solution and allowed to dry. Next, 1 µL of DI water followed by a microscopic 3×1×5/128-inch glass slide was put on each specimen. Finally, with a 500 g weight on top of it, the microscopic slide was moved back and forth a few millimeters at about 1 cm/sec for 60 seconds (FIG. 8). The results showed considerably higher flutax-1 removal from the bare latex compared to CNT-anchored one (FIG. 9). After the test, each of the two specimens was dropped in 2 mL of pure ethanol to see if they still had flutax-1 left on them. There was considerably more flutax-1 released (present) from the CNT-anchored latex compared to the bare one (FIG. 10).

Figure 11A:
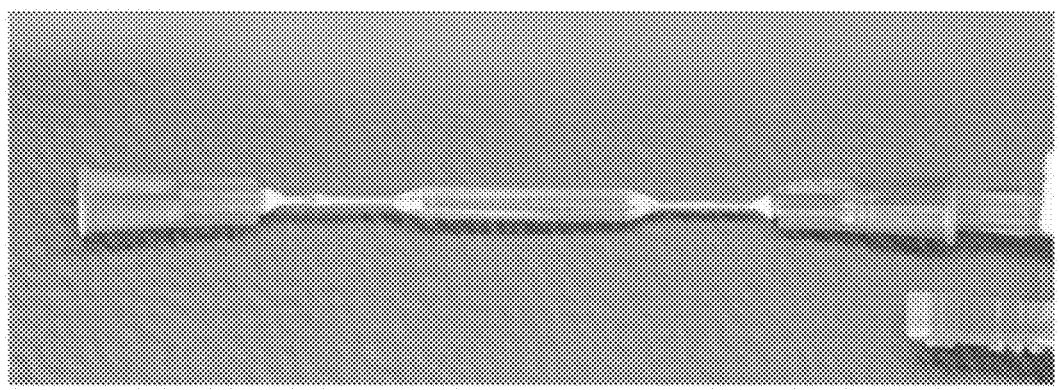
Figure 11B:
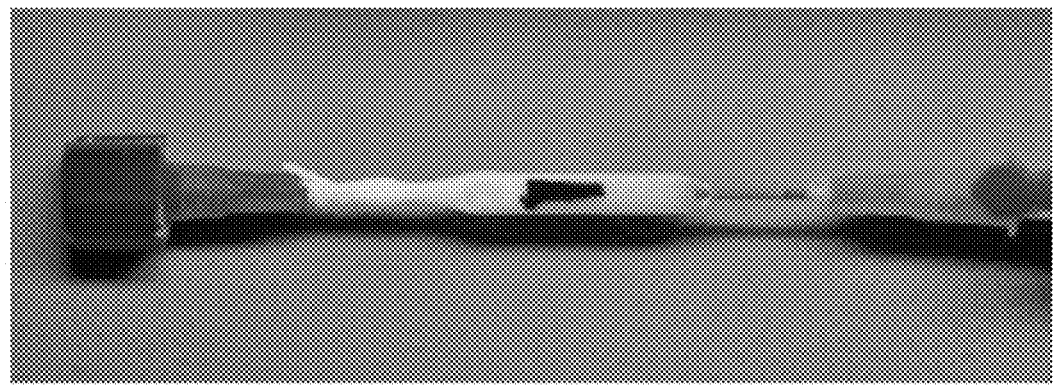

A CNT-fitted angioplasty balloon was prepared with vertically aligned CNT arrays and anchored on a polymeric layer. We started with a 20 mm-long PET angioplasty balloon (Advance Polymers, Item No. 03002016AA). This balloon was then dipped into a liquid latex compound such that the entire surface of the balloon was covered uniformly with a thin layer of latex. Before the latex layer was cured, a silicon substrate, which has as-grown CNTs on it, was placed in the inverted position onto the latex layer. After the latex layer was cured, the silicon substrate was then removed, leaving the CNTs anchored firmly on the latex layer (FIG. 11). The right length and packing density of CNTs that allow optimized drugs delivery and protection can be selected and used according to specific requirements of a particular application.

For continuous monitoring of angioplasty drug delivery, fluorescent-conjugated versions of the drugs intended for delivery, for example, flutax-1 instead of taxol, can be used. This method eliminates the need for potentially hazardous administration of a fluorescent dye intravenously through a central venous line. Illuminating can be done with a light source to accommodate the excitation of delivered fluorescent-conjugated drug. A digital camera can be used to record the imagery of emitted light. (Detter, et al. 2007 *Circulation* 116:1007-1014; Hattori, et al. 2009 *Circ Cardiovasc Imaging* 2:277-278; Hosono, et al. 2010 *Interact CardioVasc Thorac Surg* 10:476-477; Tanaka, et al. 2009 *J Thorac Cardiovasc Surg* 138:133-140; Waseda, et al. 2009 *JACC Cardiovascular Imaging* 2:604-612.)

The following studies apply Fick's second law of diffusion in a semi-infinite medium, x≥0. The concentration at the applicator (angioplasty balloon, etc.) interface is assumed constant in the first version, diminishing in the second. The first refers to the initial time-span when applicator is still touching the plaque, the second refers to post applicator removal.

One-Dimensional Semi-Infinite Slab Model of Solid-Solid Diffusion, Version I

This model assumes constant concentration at the applicator (angio balloon, etc) interface. (Perry, et al. 1963 *Chemical Engineers' Handbook*, 4$^{th}$ edition, McGraw-Hill, New York.)

$$\frac{\partial C(x,t)}{\partial t} = D\frac{\partial^2 C(x,t)}{\partial x^2} \quad (1)$$

Fick's second law of diffusion in a semi-infinite medium, $x \geq 0$.

Simplified Initial and Boundary Conditions $C(x,0)=0$ initial condition (2)

$C(0,t)=C_0$ boundary condition (3)

Simplified Analytical Solution
Laplace transform with respect to t yields, $$\int_0^\infty e^{-st}\frac{\partial C(x,t)}{\partial t}dt = D\int_0^\infty e^{-st}\frac{\partial^2 C(x,t)}{\partial x^2}dt \Rightarrow \frac{d^2 F}{dx^2} - \frac{s}{D}F = 0 \quad (4)$$

because of the initial condition $F(x,s) = (c_0/s)e^{-sx/D}$, $F(0,s) = c_0/s$ because of the boundary condition (5)

Reverse transform yields, $$C(x, t) = C_0 \left[1 - \frac{2}{\sqrt{\pi}} \int_0^{x/(2\sqrt{Dt})} e^{-\mu^2} d\mu \right]$$ (6)

for the concentration peak onwards

One-Dimensional Semi-Infinite Slab Model of Solid-Solid Diffusion, Version II

This model assumes diminishing concentration at the applicator (angio balloon, etc) interface. (Mehrer 2007 *Diffusion in Solids: Fundamentals, Methods, Materials, Diffusion-Controlled Processes*, Springer-Verlag, Berlin.)

$$\frac{\partial C(x, t)}{\partial t} = D \frac{\partial^2 C(x, t)}{\partial x^2}$$ (7)

Fick's second law of diffusion in a semi-infinite medium, $x \geq 0$.

Simplified Initial and Boundary Conditions $C(x,0) = M\delta(x)$ initial condition (8)

where M is the number of diffusing particles per unit area and $\delta(x)$ the Dirac delta function.

$$\frac{\partial C(0, t)}{\partial x} = 0 \text{ boundary condition}$$ (9)

The analytical solution is the following Gaussian equation $$C(x, t) = \frac{M}{\sqrt{\pi Dt}} \exp\left(-\frac{x^2}{4Dt}\right)$$ (10)

which at $t = 0$ reduces to $C(x, 0) = M\delta(x)$

Figure 12:
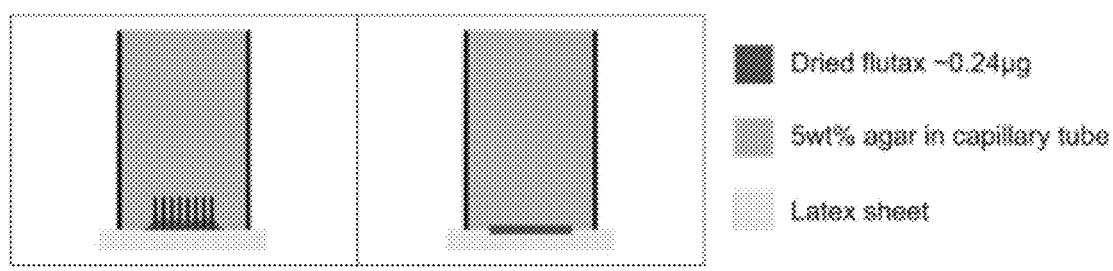
Figure 13:
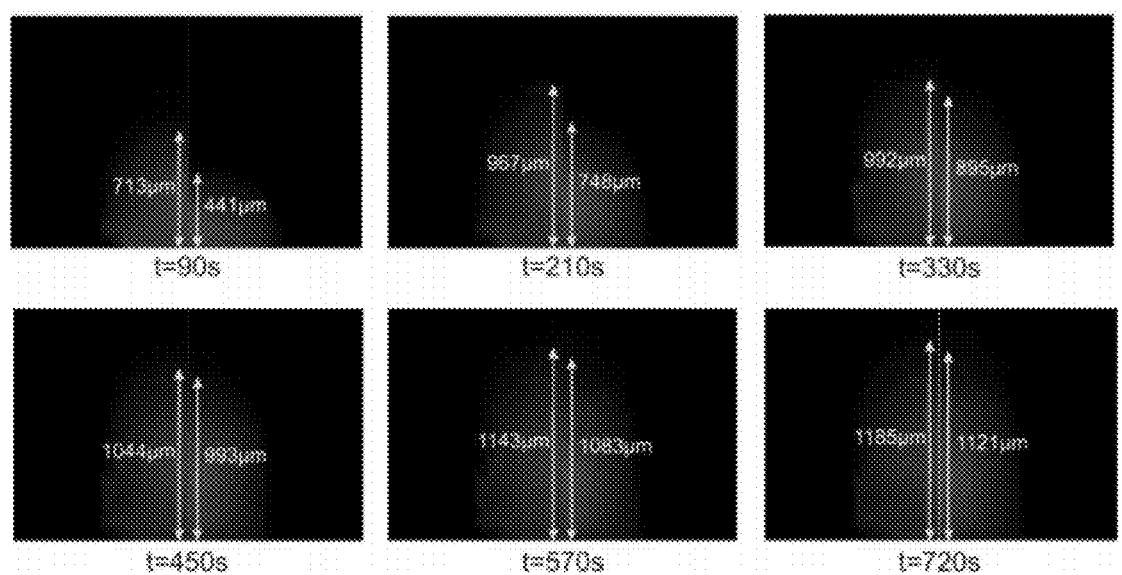
Figure 14:
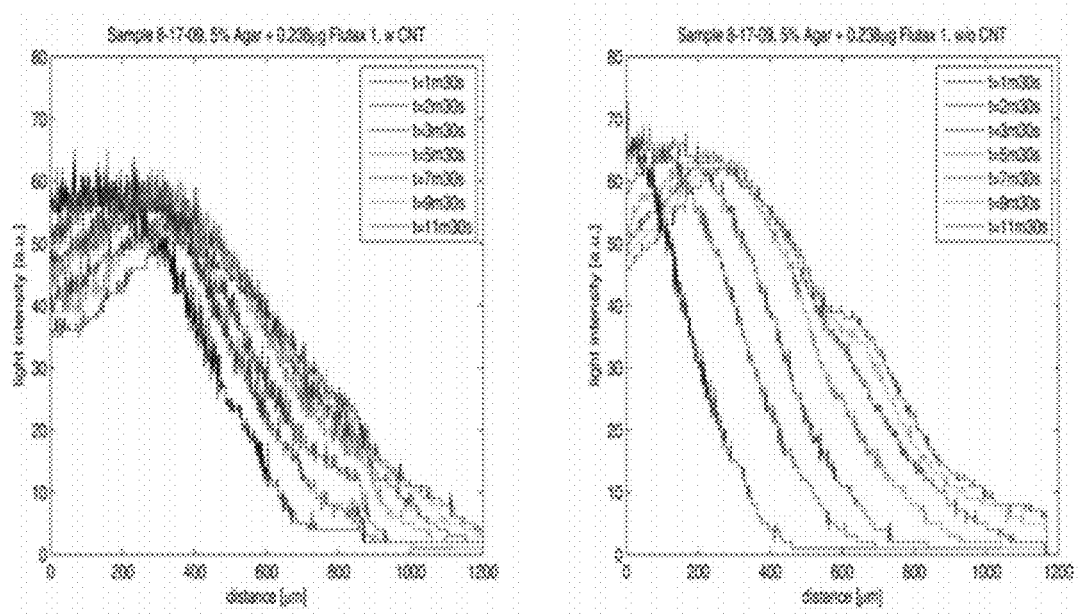

The diffusion of drugs from coated anchored CNT arrays and the pressure driven mass transfer through such structures was experimented with diffusion of flutax-1 from an anchored CNT array in agar gels and water-containing protein/lipid/cholesterol structures (including swine and chicken skin). The results indicated that flutax-1 molecules did not move appreciably in DI water, but do so in agar (in a matter of minutes) or gelatin-water-containing matrices. The results with agar gels are presented below (FIGS. 12-14), and fit reasonably with the simple theoretical model. The diffusion from the anchored CNT array was compared with simple diffusion from a thin strip of dried flutax on a bare polymeric sheet (the geometries of both cases examined are illustrated in FIG. 12).

The diffusion process was modeled with Fick's second law, assuming one-dimensional diffusion and neglecting the melting time of the dried flutax in comparison with the diffusion time within the agar (which is supported by experimental data). Schematic description of the geometry for both examined cases is presented in FIGS. 15(b) and (c).

The model for the case of thin layer of flutax ($L_1/L \ll 1$) consists of one-dimensional diffusion within the agar gel $$\frac{\partial C(x, t)}{\partial t} = D \frac{\partial^2 C(x, t)}{\partial x^2},$$

and constant concentration $C(x=0,t)=C_0$ and no flux $\partial C(x=0, t)/\partial x = 0$ boundary conditions at $x=0$ and $x \to \infty$, respectively. A classical solution for this problem exists in the literature, and is defined as $$C(x, t) = C_0 \left[1 - \text{erf}\left(\frac{x}{2\sqrt{Dt}}\right)\right].$$

For the case of flutax positioned within a CNT array (FIG. 15c) $L_2$ cannot be neglected in comparison with L, and two regions of diffusion are modeled, the agar region and the CNT region. Since the entire length of the CNT array is coated with flutax at t=0, the initial condition is now $$C(x, t = 0) = \begin{cases} 0, & x > L_2 \\ C_0, & x < L_2. \end{cases}$$

Utilizing the one-dimensional case, the reduction in available area for the diffusion process within the CNT region can be modeled by reducing the value of the diffusion coefficient proportionally to the reduction in surface area and the initial concentration $C_0$ can be estimated from the amount of flutax and the available void space within the CNT array.

Figure 15:
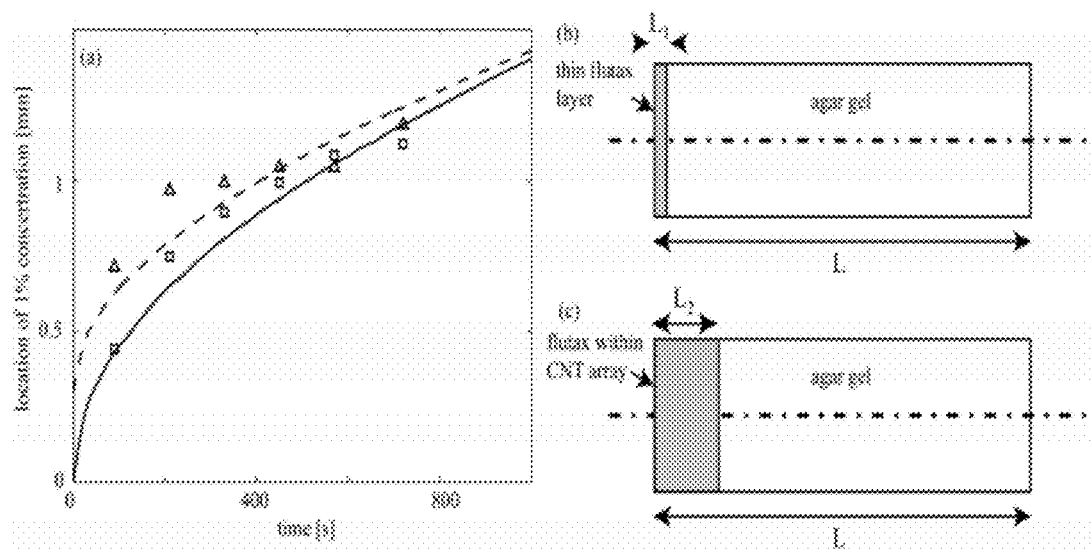

FIG. 15 presents the numerical solution of the models and the experimental data for thin flutax layer (squares and smooth line) and flutax within CNT array (triangles and dashed line). The general trends of the diffusion are predicted reasonably. The main effect of the CNT array is to change the initial conditions of the diffusion and thus the differences between both cases are expected to decrease as t increase, which is indeed observed in experimental data in accordance with the model.

EXAMPLES

Experimental Methods

CNT arrays growth. The vertically aligned multi-walled carbon nanotube arrays used in this study were grown using thermal chemical vapor deposition on silicon wafer substrates. These wafers were coated with 10 nm aluminum oxide buffer layer and 1 nm iron catalyst layer using electron beam evaporator (Temescal BJD 1800) and diced into 1×1 cm samples. The growth itself was performed in a 1-inch diameter quartz tube furnace (Lindberg/BlueM Single Zone Tube Furnace) under the 490 standard cubic centimeters per minute (sccm) ethylene gas (Matheson 99.999%) and 210 sccm hydrogen gas (Airgas 99.999%) at a temperature of 750° C. and a pressure of 600 torr. The flow rate and pressure of the gases was maintained by an electronic mass flow controller (MKS πMFC) and a pressure controller (MKS πPC). The overall growth quality, including the length of the array, was characterized under scanning electron microscope (ZEISS LEO 1550VP).

Anchored CNT on flat surface. A thin layer of uncured polymer (e.g., PDMS) was spin-coated (SCS G3 spin coater) onto a flat rigid substrate. The thickness of the polymer layer can be controlled by varying the speed (rpm) and dwell time of the spinner. As-grown carbon nanotube arrays were manipulated by handling their growth substrate, inverted and then inserted into the spin-coated polymer layer. The whole assembly was subsequently cured, usually by heat at elevated temperature (e.g., about 80° Celsius). The CNT's growth substrate could then be easily removed after the polymer layer is fully cured. By controlling the polymer layer thickness and CNTs length, the depth of anchoring of the CNTs into the flexible polymer layer may be controlled.

Anchored CNT on balloon. A 20 mm-long PET angioplasty balloon (Advance Polymers 03002016AA) was used as a platform. This balloon was then dipped into a liquid latex compound so that the entire surface of the balloon was covered uniformly by a thin layer of latex. Before the latex layer was cured, CNTs attached to a silicon substrate were inverted then placed into the latex layer. The whole assembly was subsequently cured by leaving it in air at room temperature for 24 hours. After the latex layer was cured, the silicon substrate was then removed, leaving the CNTs anchored firmly on the latex layer on the balloon.

Flutax-1 and uranine attachment on CNT. Two types of dye were used in these experiments: the uranine (sodium fluorescein, Sigma Aldrich 67884) that represents the hydrophilic drugs and flutax-1 (Tocris Bioscience 2226) that represents the hydrophobic drugs. Since the carbon nanotubes are highly hydrophobic, both fluorescein sodium and flutax-1 were dissolved in pure ethanol (Sigma Aldrich E7023), so that both dyes could wick into the interstices of the CNT specimen. The same amounts of both fluorescein sodium and flutax-1 were placed by successively dropping small volumes in each specimen and letting them dry in air at room temperature.

Diffusion measurement. Diffusion of flutax-1 from an anchored CNT array was measured in 5% agar gels (Sigma Aldrich 17209) in water. The agar gels were placed inside a 1450 μm OD×860 μm ID glass capillary tube (Clay Adams 4614). The anchored CNT array was then placed flush to the tip of the capillary tube. To determine the diffusion profile of the flutax-1 from the CNT array into the agar gels, time lapsed photographs were taken by fluorescent microscope (Nikon Eclipse TE2000-S). The diffusion profile was then determined from the fluorescence intensity captured in these photographs.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A method for delivering an agent to a patient in situ, comprising:
    (a) providing an implantable device having a surface anchored thereon a plurality of multi-walled carbon nanotubes;
    (b) depositing the agent to the plurality of multi-walled carbon nanotubes such that the agent is non-covalently associated with the plurality of multi-walled carbon nanotubes;
    (c) placing the implantable device at a target location in the patient's body; and
    (d) allowing the agent to diffuse from the plurality of multi-walled carbon nanotubes, thereby delivering the agent in situ.

2. The method of claim 1, wherein the agent is a pharmaceutical agent capable of providing a therapeutic effect on the patient.

3. The method of claim 1, wherein the agent is a diagnostic agent capable of providing a detectable signal or image indicating a biologically relevant state of the subject.

4. The method of claim 1, wherein the agent comprises an aromatic moiety.

5. The method of claim 4, wherein the aromatic moiety comprises a heteroatom selected from N, O or S.

6. The method of claim 4, wherein the aromatic moiety comprises two or more fused rings.

7. The method of claim 4, wherein the agent has a molecular weight from about 130 to about 1500.

8. The method of claim 1, further comprising monitoring delivery of the agent in situ.

9. The method of claim 1, wherein the plurality of multi-walled carbon nanotubes are not surface functionalized.

10. The method of claim 1, wherein the implantable device is an angioplasty balloon.

11. The method of claim 10, wherein the angioplasty balloon is anchored uniformly with the plurality of multi-walled carbon nanotubes without surface functionalization.

* * * * *